United States Patent [19]

Portnoff et al.

[11] Patent Number: 5,583,052
[45] Date of Patent: Dec. 10, 1996

[54] FORMULATION PREPARATION DEVICE

[75] Inventors: Joel B. Portnoff, Langhorne, Pa.; Royden M. Coe, Bordentown, N.J.; John Grimm, Schnecksville, Pa.; Kenneth Raines, Bethlehem, Pa.; Joel Bartholomew, Danielsville, Pa.

[73] Assignees: The Liposome Company, Inc., Princeton, N.J.; B. Braun Medical, Inc., Bethlehem, Pa.

[21] Appl. No.: 447,660

[22] Filed: May 23, 1995

Related U.S. Application Data

[63] Continuation-in-part of Ser. No. 248,075, May 23, 1994, abandoned.

[51] Int. Cl.[6] ............................................. G01N 1/10
[52] U.S. Cl. ........................................ 436/180; 422/103
[58] Field of Search .............................. 422/103; 604/82, 604/83, 411; 436/180

[56] References Cited

U.S. PATENT DOCUMENTS

| | | | |
|---|---|---|---|
| 2,409,343 | 10/1946 | Curtis | 128/214 |
| 4,098,275 | 7/1978 | Consalvo | 128/214 R |
| 4,244,378 | 1/1981 | Brignola | 128/766 |
| 4,475,914 | 10/1984 | Portnoff | 604/414 |
| 4,522,803 | 6/1985 | Lenk et al. | 424/1.1 |
| 4,588,578 | 5/1986 | Fountain et al. | 424/1.1 |
| 4,655,763 | 4/1987 | Maclolm et al. | 604/414 |
| 4,721,612 | 1/1988 | Janoff et al. | 424/1.1 |
| 4,729,401 | 3/1988 | Raines | 137/512 |
| 4,787,898 | 11/1988 | Raines | 604/411 |
| 4,823,833 | 4/1989 | Hogan et al. | 137/567 |
| 4,915,688 | 4/1990 | Bischoff et al. | 604/83 |
| 4,975,282 | 12/1990 | Cullis et al. | 424/450 |
| 5,008,050 | 4/1991 | Cullis et al. | 264/4.3 |
| 5,012,845 | 5/1991 | Averette | 141/329 |
| 5,030,453 | 7/1991 | Lenk et al. | 424/450 |
| 5,037,390 | 8/1991 | Raines et al. | 604/83 |
| 5,059,421 | 10/1991 | Loughrey et al. | 424/417 |
| 5,077,056 | 12/1991 | Bally et al. | 424/450 |
| 5,100,662 | 3/1992 | Bolcsak et al. | 424/88 |
| 5,169,637 | 12/1992 | Lenk et al. | 424/450 |

FOREIGN PATENT DOCUMENTS

| | | | |
|---|---|---|---|
| 0320503 | 6/1989 | European Pat. Off. | B47C 3/02 |
| 3404989 | 8/1985 | Germany | A61M 5/00 |
| 7-51385 | 2/1995 | Japan | A61M 39/00 |
| 86/01102 | 2/1986 | WIPO . | |

OTHER PUBLICATIONS

Bangham, et al., "Diffusion of Univalent Ions Across the Lamellae of Swollen Phospholipids", J. Mol. Boil. 13:228, 1965.

Cullis, et al., "Liposomes as Pharmaceuticals", in: *Liposomes, From Biophysics to Therapeutics* (M. Ostro, ed.,), Marcek Dekker, New York (1987), pp. 39–72.

Deamer, et al., "Liposome Preparation: Methods and Mechanisms" in: *Liposomes* (M. Ostro, ed.), Marcel Dekker, New York, (1983), pp. 27–51.

Gruner, "Materials Properties of Liposomal Bilayers", in:*Liposomes, From Biophysics to Therapeutics,* (M. Ostro, ed.) Marcel Dekker, New York 1987, pp. 1–38.

Papahadjopoulos, et al., "Phospholipid Model Membranes I. Structural Characteristics of Hydrated Liquid Crystals," BBA, 135:624, 1967.

*Primary Examiner*—Jill Warden
*Assistant Examiner*—Alexander Markoff
*Attorney, Agent, or Firm*—Kenneth B. Rubin

[57] ABSTRACT

A formulation preparation device is provided herein which contains a valve assembly, transfer spikes, syringe port and tube, these components being interconnected so as to provide for controlled fluid flow between the spikes and port, through the assembly, in specific directions only. The device has an enclosed, sterilizable, gripable housing and can be used to mix combine fluids in reproducible and predetermined proportions. Combination is accomplished aseptically, avoiding contact between the device's operator and the fluids and the substances combined. Biologically active compounds can be combined with one or more fluids, including such aqueous liposome suspensions, using the device. A formulation preparation kit containing, in addition to the device, the fluids and compounds to be formulated is thus also provided herein; methods of using the device to prepare such formulations are further provided herein.

15 Claims, 3 Drawing Sheets

FORMULATION PREPARATION DEVICE

This application is a continuation-in-part of application Ser. No. 08/248,075, filed on May 23, 1994, now abandoned.

This invention is directed to a device for preparing fluid-containing formulations including, but not limited to, formulations also containing liposomes and biologically active agents. Fluids can be mixed aseptically, and in reproducibly defined quantities, by the device.

Combining fluids, especially those containing chemical compositions such as pharmacologically or biologically active agents, is a frequently followed practice in the medical, such as, but not limited to, the dental and chemical fields, amongst others, and is generally designed to provide the fluids in a form more suited to their intended end use. Such combinations should generally be available for use in the form in which they are prepared, but can become unstable over time, with separation of component fluids and compositions. Fluid combinations can also become microbiologically contaminated when removed from aseptic storage. Accordingly, increasing the utility of composition-fluid formulations may require that the combination of the composition and the fluid be delayed to as close to the time of the formulation's intended use as possible.. Provision of an easy-to-operate device that can be successfully manipulated by end users of the formulations, such as medical personnel, including, but not limited to, doctors, nurses, technicians, pharmacists, and dentists, and chemists, would allow such personnel to control the time a formulation is made relative to the time the formulation is to be employed.

Fluid-containing vials and a composition-containing receptacle, provided along with the device in the preparation kit of this invention, can readily be attached to the device's infusion and transfer spikes; the device can then readily be manipulated to prepare formulations. Further contact risk to the operator can be minimized by disposing the device after it is used, without removing the vials from the device's spikes.

Formulations useful in the medical and laboratory chemical fields, amongst others, can be prepared with the device of this invention. A particularly useful area for the device is in the preparation of pharmaceutical formulations containing biologically active agents, such as liposomal formulations. Liposomes are self-assembling structures consisting of one or more closed lipid bilayers, each of which surrounds a compartment containing water. Each of the bilayers contains two opposing monolayers of amphipathic lipid molecules, the hydrophilic headgroup portions of which are oriented towards the surrounding aqueous solution and the hydrophobic fatty acid chains regions of which are arrayed in the bilayer interior (see, for example, S. M. Gruner, "Materials Properties of Liposomal Bilayers," in: *Liposomes, From Biophysics to Therapeutics* (M. Ostro, ed.), Marcel Dekker, New York (1987), pp. 1–38; D. Deamer and P. Uster, "Liposome Preparation: Methods and Mechanisms," in: *Liposomes* (M. Ostro, ed.), Marcel Dekker, New York (1983), pp. 27–51). Liposomal biologically active agents can have an enhanced therapeutic index by increasing the agents' efficacies, minimizing associated toxicities, or both; furthermore, liposomes tend to be absorbed by an animals' reticuloendothelial system, and are hence very often directed to the sites of intracellular infection in the animal (see, for example, P. Cullis et al., "Liposomes as Pharmaceuticals," in: *Liposomes, From Biophysics to Therapeutics* (M. Ostro, ed.), Marcel Dekker, New York (1987), pp. 39–72).

Ionizable biologically active agents can be loaded into a liposome by establishing an electrochemical potential gradient, for example, a pH gradient, across the liposome's outermost lipid bilayer and then adding the agents to the aqueous solution external to the liposome (see, for example, M. Bally et al., U.S. Pat. No. 5,077,056, issued Dec. 31, 1991; M. Bally et al., International Publication No. WO86/01102.). The ionizable agents, for example, antineoplastic agents such as doxorubicin, are then loaded into the liposome by the gradient. This invention's device is especially useful in connection with biologically active agents and liposomes in that the agent's loading can be delayed until immediately prior to the liposome's use, thus minimizing leakage of the agent from the liposome.

SUMMARY OF THE INVENTION

This invention provides a formulation preparation device, comprising: (I) a valve assembly; (ii) a first transfer spike; (iii) a second transfer spike; (iv) a third transfer spike; (v) a syringe port; (vi) a tube; and (vii) a sterilizable, gripable housing.

The valve assembly comprises: (I) a first passage having a first aperture, a second aperture and a bore connecting the first and second apertures; (ii) a second passage having a third aperture, a fourth aperture and a bore connecting the third and fourth apertures; (iii) a third passage having a fifth aperture, a sixth aperture and a bore connecting the fifth and sixth apertures; and (iv) a main body having a central cavity comprising a first valve disc, a second valve disc and the second, fourth and sixth apertures. The first transfer spike comprises: (I) a beveled point having a double-lumened channel connected to the first aperture; and (ii) a fourth passage having a seventh aperture in the channel, an eighth aperture and a conduit connecting the seventh and eight apertures. The second transfer spike comprises: (I) a beveled point having a double-lumened channel connected to a ninth aperture opposite the point; (ii) a first hydrophobic air filter sealed into the ninth aperture; and (iii) a fifth passage having a tenth aperture in the channel, an eleventh aperture and a bore connecting the tenth and eleventh apertures. The tube connects the eighth and eleventh apertures. The syringe port comprises an opening, which preferably, but not necessarily comprises a syringe locking fitting, and a sixth passage connecting the opening and the third aperture. The third transfer spike comprises: (I) a beveled point having a double-lumened channel connected to the fifth aperture; and (ii) a seventh passage having an inner opening in the bore, an outer opening, a channel connecting the inner and outer openings and a second hydrophobic air filter sealed into the outer opening. Each of the transfer spikes can comprise a collar which is positioned on the spikes between the beveled point and the outer surface of the housing; the device can also comprise a fourth transfer spike.

When a syringe is inserted into the receptacle and the syringe plunger is aspirated downward, the first and second valve discs are positioned in the valve assembly central cavity such that the first and third apertures are open and the fifth aperture is closed; and when the Syringe plunger is infused upward, the first and second valve discs are positioned in the valve assembly central cavity such that the third and fifth apertures are open and the first aperture is closed.

Also provided herein is a formulation preparation kit which comprises: the device, a first vial comprising a first fluid, a second vial comprising a second fluid and a third vial, wherein the first and second fluids are combined by the device and wherein the fluid combination is then injected by the device into the third vial so as to form a formulation comprising the fluid combination and the contents of the third vial. Preferably, but not necessarily, the first fluid comprises a liposome which comprises an aqueous buffer having a first pH; more preferably, the liposome is a unilamellar liposome and the aqueous buffer is a citric acid buffer. Preferably, the second fluid is an aqueous buffer having a second pH which is acidic or basic with respect to the first pH and wherein the third vial contains an ionizable biologically active agent.

Preferably, the third vial contains a chemical compound, including, but not limited to: a biologically active agent, dental agent, dye, epoxy or chemical reagent. More preferably, the chemical is a biologically active agent selected from the group consisting of therapeutic, diagnostic, dental, cosmetic, nutritional and prophylactic agents. Still more preferably, the biologically active agent is a therapeutic agent selected from the group consisting of anti-arthritic, anti-arrhythmic, antibacterial, anticholinergic, anticoagulant, antidiuretic, antidote, antiepileptic, antifungal, anti-inflammatory, antimetabolic, antimigraine, antineoplastic, antiparasitic, antipyretic, antiseizure, antisera, antispasmodic, analgesic, anesthetic, beta-blocking, biological response modifying, bone metabolism regulating, cardiovascular, diuretic, enzymatic, fertility enhancing, growth-promoting, hemostatic, hormonal, hormonal suppressing, hypercalcemic alleviating, hypocalcemic alleviating, hypoglycemiC alleviating, hyperglycemic alleviating, immunosuppressive, immunoenhancing, muscle relaxing, eurotransmitting, parasympathomimetic, sympathomimetic, plasma extending, plasma expanding, psychotropic, thrombolytic and vasodilating agents. Preferably, the therapeutic agent is an antineoplastic agent selected from the group consisting of anthracycline antibiotics, vinca alkaloids, purine or pyrimidine derivatives or alkylating agents.

Most preferably, the first fluid comprises a unilamellar liposome having an average diameter of greater than about 50 nm and comprising a citric acid buffer having a pH of from about 3.5 to about 4.5; the second fluid comprises a carbonate buffer; and the third vial comprises an ionizable biologically active agent, preferably an anthracycline antibiotic antineoplastic agent selected from the group consisting of doxorubicin, daunorubicin and epirubicin, and more preferably doxorubicin. The agent, the liposome and the carbonate buffer are combined so that the liposome is suspended in the carbonate buffer and the agent is entrapped in the liposome.

Further provided herein is a method of preparing a formulation with the device, the method comprising: (I) attaching a first vial containing a first fluid to the first transfer spike, a second vial containing a second fluid to the second transfer spike and a third vial to the third transfer spike; (ii) inserting a syringe into the syringe receptacle and aspirating the plunger of the syringe downward so as to combine the first and second fluids; and infusing the plunger of the syringe upward so that the fluid combination flows into the third vial so as to form a formulation comprising the combination and the contents of the third vial. Preferably, the first vial comprises a unilamellar liposome having an average diameter of greater than about 50 nm and a citric acid buffer having a pH of from about 3.5 to about 4.5, the second vial comprises a carbonate buffer and the third vial comprises doxorubicin. The doxorubicin, the liposome and the carbonate buffer are combined so that the liposome is suspended in the carbonate buffer and the doxorubicin is entrapped in the liposome.

DETAILED DESCRIPTION OF THE INVENTION

This invention provides a formulation preparation device, as shown in FIG. 1, containing: a valve assembly (A); a first transfer spike (B); a second transfer spike (C); a third transfer spike (D); a syringe port (E); a tube (F); and a sterilizable, gripable housing (G). When a syringe is inserted into the syringe port and the syringe plunger is aspirated downward, fluid flows from the first and second transfer spikes (B, C) through the assembly (A) and into the syringe, but fluid does not then flow into the third transfer spike (D). When the syringe plunger is infused upward, fluid flows from the syringe through the assembly (A) and into the third transfer spike (D), but fluid does not then flow into the other spikes (B, C).

The valve assembly (A) comprises: (I) a first passage having a first aperture, a second aperture and a bore connecting the first and second apertures; (ii) a second passage having a third aperture, a fourth aperture and a bore connecting the third and fourth apertures; (iii) a third passage having a fifth aperture, a sixth aperture and a bore connecting the fifth and sixth apertures; and (iv) a main body having a central cavity comprising a first valve disc, a second valve disc and the second, fourth and sixth apertures. "Connection" or "connecting" means that the components of the device are put together by techniques that are well known to ordinarily skilled artisans and designed to allow fluids to pass through the device without leaking therefrom.

The valve assembly (A) is any valve assembly which: has three passages and two valve discs; permits fluid flow only between the first and second passages, but not between either of these and the third passage, when under a negative pressure, such as when a connected syringe is aspirated; and which permits fluid flow only between the second and third passages, but not between either of these and the first passage, when under a positive pressure, such as when a connected syringe is infused.

Figure 1A:
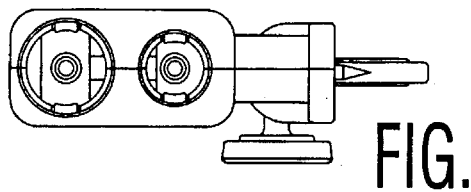
FIG. 1. A: Top view of the invention; B: side view; C: front view; D: cross-sectional view.
Figure 1B:
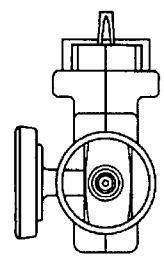
Figure 1C:
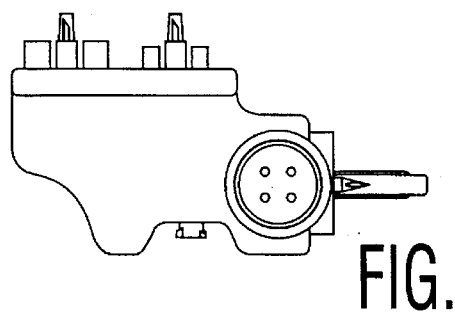
Figure 1D:
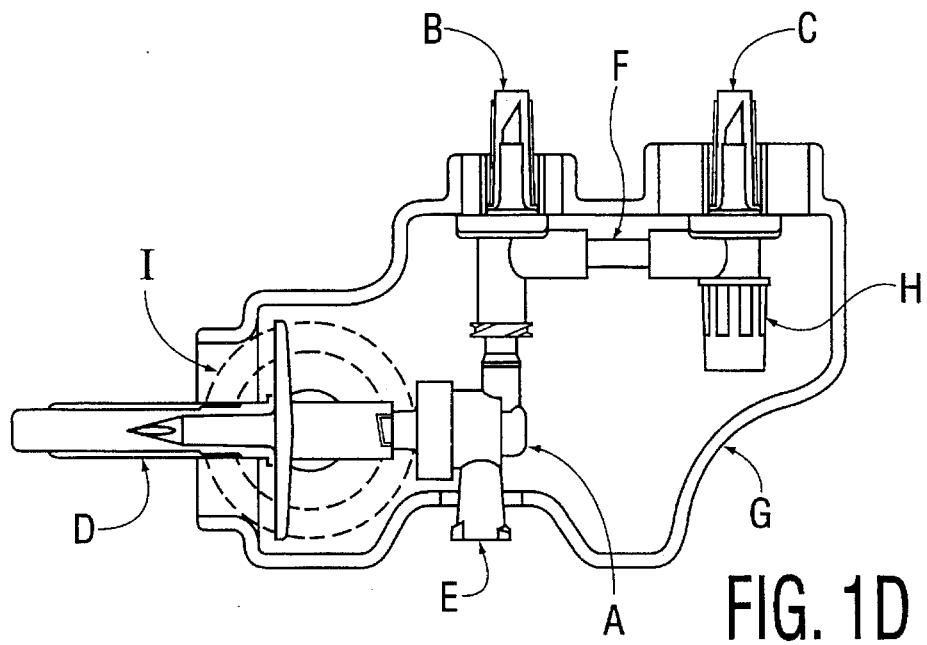
Figure 2:
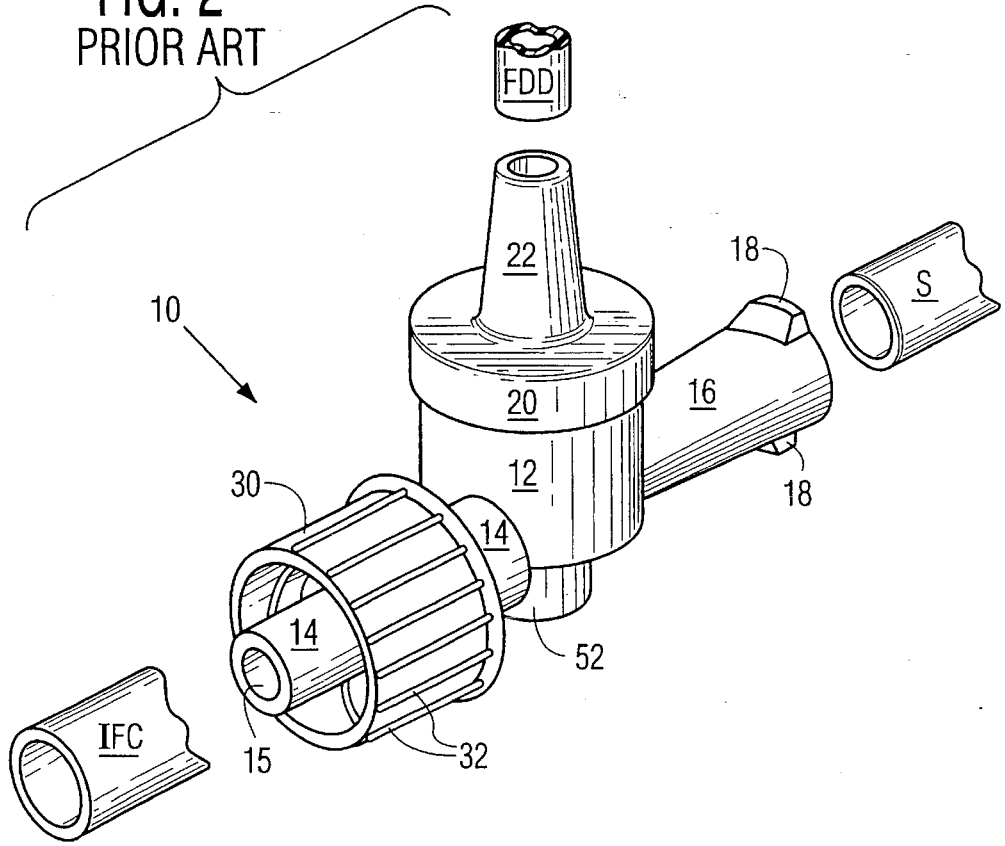
FIG. 2. Perspective view of the valve assembly shown in FIG. 1 and in U.S. Pat. No. 4,729,401.
Figure 3:
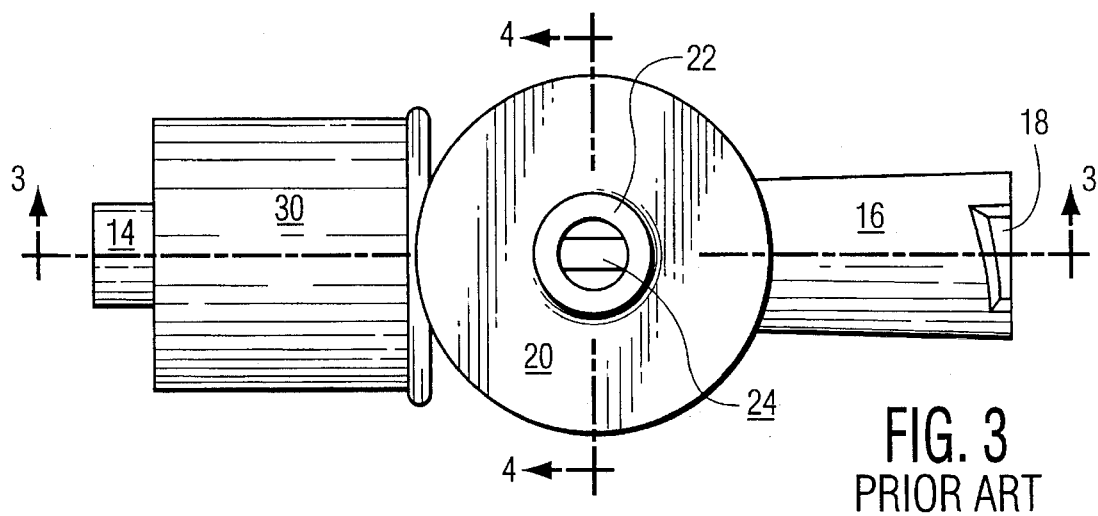
FIG. 3. Top plan view of the invention of the valve assembly shown in FIG. 1 and in U.S. Pat. No. 4,719,401.
Figure 4:
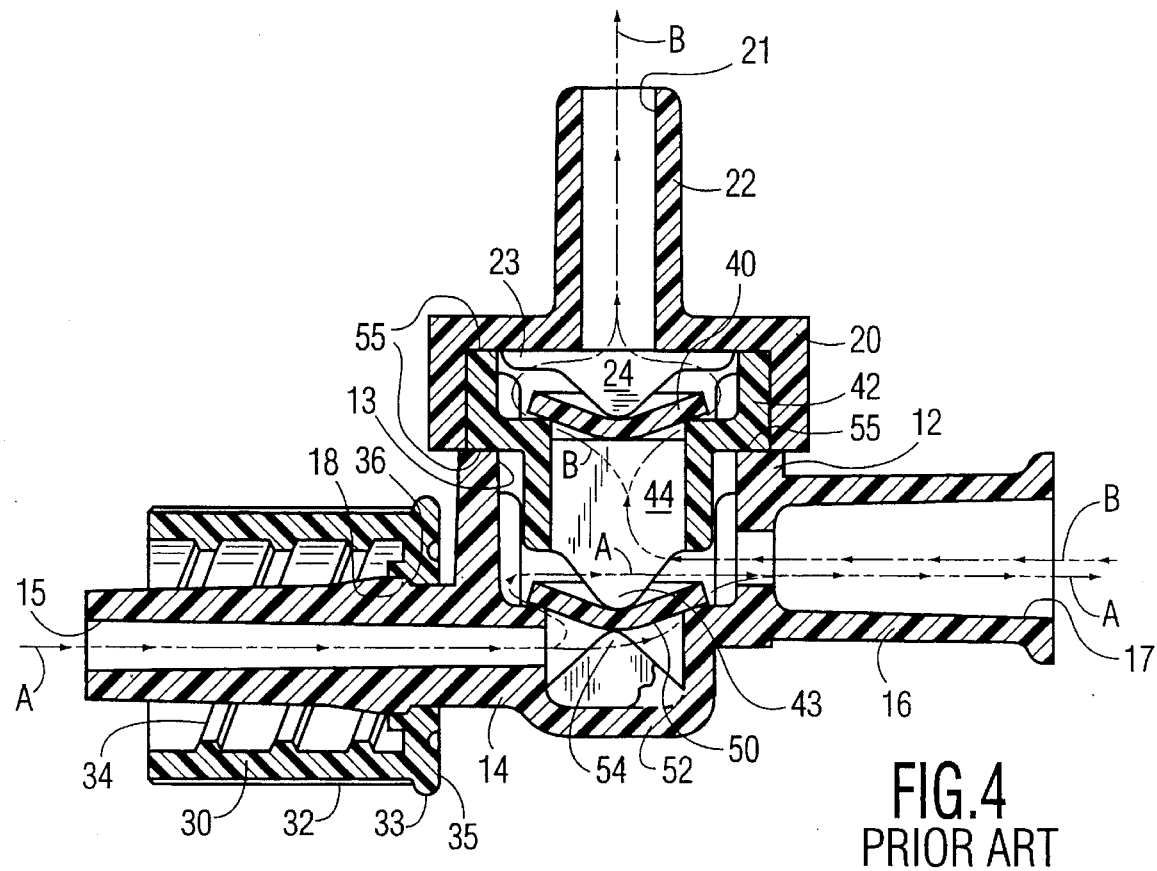
FIG. 4. Side elevation view in cross-section taken generally along the lines 3—3 of FIG. 3.
Figure 5:
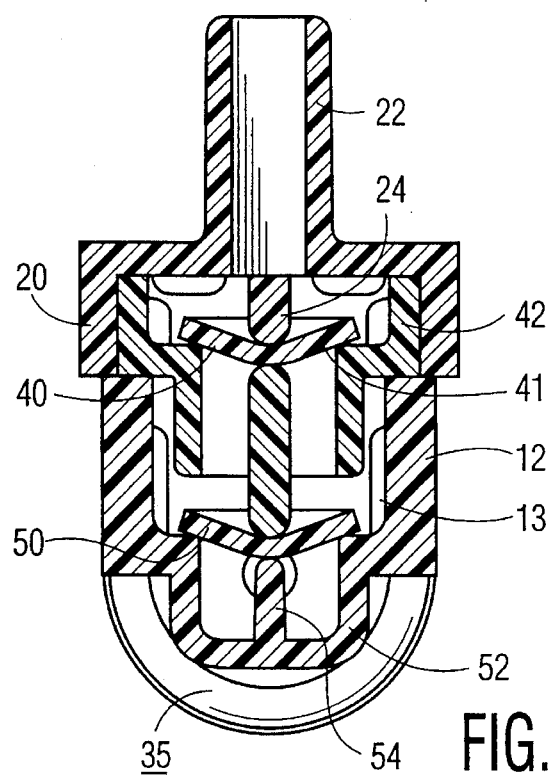
FIG. 5. End elevation view taken generally along the lines 4—4 of FIG. 3.

Preferably, the valve assembly is that described in U.S. Pat. No. 4,729,401, the contents of which are incorporated herein by reference, and depicted in FIGS. 2–5 herein from the '401 patent. The valve assembly comprises a first and a second co-axial check valve ("valve discs"). The valve's main body (reference number 12 in FIG. 3) has two extensions, 14 and 16, projecting therefrom. These extensions provide for passageways 15 and 17, respectively (see, FIG. 4). The inner ends of these passageways 15 and 17 come together in the central cavity 13 within the main body. A top cap 20 is provided for closing the open area of the central cavity; this cap is connected to the main body through intermediate element 42, which is a central valve disc support structure provided with a valve seat 41, a valve disc triangular support and pressure point 43 mounted at the lower end of cross-ring 44. The top cap 20 is provided with a cross-rib 23 having a triangular pressure point 24 at the middle thereof. An output passageway 21 is provided through the cap projection 22. During the assembly of this aspiration valve assembly, appropriate resilient and flexible valve discs 40 and 50 are placed within the main body 12, along with the central support structure 42. Then, sonic welding or sealing is used along the areas 55 to permanently affix the three basic components together in their assembled relationship. Luer ears (18) may be provided on the projection 16 for appropriate connection to other fluid transfer apparatii; likewise, the output projection 22 is suitably tapered externally thereof for connection. Similarly, an input fluid conduit may be attached to the input projection (14) of the assembly. A coupling 30 may be provided for this projection, with the coupling having internal threads 34 and external ribs 32. A base flange 33 is provided circumferentially of this coupling, and an end 35 encloses an inner end thereof. This coupling may be retained upon projection 14 by the shoulder 18 which engages with the recess offset 36 of the coupling. In order to positively retain the valve disk (50) in position, the main body (12) is provided with a depending bottom (52), having a pressure point (54) mounted vertically thereon. The lower valve disk is retained in operative position by the opposite pressure points 43 and 54, while the upper valve disk (40) is suitably retained by the upper mid surface of rib 44 and the opposite pressure point (24).

The first transfer spike (B) comprises: (I) a beveled point having a double-lumened channel connected to the first aperture; and (ii) a fourth passage having a seventh aperture in the bore, an eighth aperture and a conduit connecting the seventh and eight apertures. The second transfer spike (C) comprises: (I) a beveled point having a double-lumened channel connected to a ninth aperture, the aperture being at the end of the channel opposite the point; (ii) a first hydrophobic air filter (H) sealed into the ninth aperture; and (iii) a fifth passage having a tenth aperture in the channel, an eleventh aperture and a bore connecting the tenth and eleventh apertures. The hydrophobic air filter (H) allows air to travel between the bore and the external environment; such air passage equalizes the pressure inside and outside the bore, and allows fluid to pass through the bore with minimal impedance. The filter (H) permits the passage of air, but prevents the passage of airborne particles, such as microbes. It is preferably a 0.45 micron bacterial depth filter (obtainable from Pall, Gore, Gelman and Millipore, amongst other vendors) that is hydrophobic, i.e., its composition inhibits absorption of fluids by the filter. Accordingly, fluid withdrawn from the containers will pass through the transfer spikes without being absorbed onto the filter. The filter (H) is "sealed" into the aperture so as to prevent air leakage through the seal and into the bore; air entering the device therefore has to pass through the filter; preferably, the sealing is by friction fit.

A tube (F) connects the eight and eleventh apertures, and thereby allows fluid to flow between the second and first transfer spikes. The syringe port (E) comprises an opening which preferably, but not necessarily, comprises a syringe locking fitting and a sixth passage connecting the opening and the third aperture. "Ports" are portals, gateways or other structures to which an apparatus that can be used to aspirate and infuse fluids can be attached. "Syringes" are any syringe now known, or later developed, that can be used to aspirate, combine and infuse fluids in connection with this invention's device and include, without limitation: Asepto, Luer and control syringes. Luer syringes are the presently preferred type of syringe used to prepare formulations with the device. A "luer syringe" is a syringe primarily used for hypodermic and intravenous administration, and comprises a tip and a locking acceptor generally suited for securing a needle to the tip. Accordingly, a syringe port "locking fitting," which is a fitting designed to hold a syringe in place in the device and is preferably a fitting designed to encompass the luer syringe tip and to secure the syringe to the device.

The third ("infusion") transfer spike (D) comprises: (I) a beveled point having a double-lumened channel connected to the fifth aperture; and (ii) a seventh passage having an inner opening in the channel, an outer opening, a bore connecting the inner and outer openings and a second hydrophobic air ("venting") filter (I) sealed into the outer opening. This second filter is a venting filter and is preferably a 0.2 micron bacterial depth filter (obtainable from such vendors as Pall, Gelman and Millipore). The filter is preferably "sealed" into the aperture by way of solvent bonding between the filter's housing and the aperture.

Accordingly the device comprises a valve assembly (A), three transfer spikes (B, C, D) and a port (E) having seven passages and eleven apertures. These passages are apportioned amongst the device's components as follows:

| Passage | Component | Aperture | Component |
|---------|-----------|----------|-----------|
| 1 | A | 1 | A |
| 2 | A | 2 | A |
| 3 | A | 3 | A |
| 4 | B | 4 | A |
| 5 | C | 5 | A |
| 6 | E | 6 | A |
| 7 | D | 7 | B |
| — | — | 8 | B |
| — | — | 9 | C |
| — | — | 10 | C |
| — | — | 11 | C |

The device of this invention is "ergonomic," that is, the housing (G) is such that it can be gripped in the hand of its operator such that it can be manipulated, turned, shaken and otherwise handled by the operator without having to be rested on a surface. Preferably, the first and second transfer spike (B, C) beveled points project from the top surface of the housing (G), as the device is oriented in its operator's hand with the syringe port being in the bottom of the device, and the third transfer spike (D) point projects from a side surface. The tube (F) and valve assembly (A) are contained within the housing (G); the first and second filters (H, I) are preferably, but not necessarily, also contained within the housing (G). The housing (G) can have a transparent surface, oriented when the device is in use such that the transparent surfaces faces the operator; such a surface allows the device's operator to observe passage of fluids through the device; optionally, the fluids mixed can contain coloring agents, to ease observation.

The device's components and housing are made from materials that are generally accepted as suitable in field, for example, the preparation of pharmaceutical formulations, in which the device is to be used. Suitable materials can be selected by ordinarily skilled artisans given the use for which the device is intended and the teachings of this invention; such materials are selected according to a number of criteria including, but not limited to: the ability to withstand sterilization conditions. For example, the presently preferred materials for constructing the device's structural components include such thermoplastics as ABS, polypropylene and polycarbonate.

The valve assembly (A), transfer spikes (B, C, D), tube (F) and syringe port (E) are interconnected so as to permit fluid passage in specified directions, within the device. When the plunger of a syringe attached to the port (E) is aspirated downward, fluid is withdrawn from a vial attached to the first transfer spike (B) and flows into the syringe through the valve assembly (A). The first and second valve discs (for example 40 and 50 in FIG. 5) are positioned as the plunger is aspirated downward such that the first disc does not block fluid flow through the valve assembly (A) while the second valve disc does block fluid flow into the third transfer spike (D). As fluid is withdrawn from the vial attached to the first transfer spike (B), fluid flows from a container attached to the second transfer spike (C), through the tube (F) and into the container attached to the first transfer spike (B), replacing fluid withdrawn therefrom; fluid can flow into and out of the vial simultaneously through the double-lumened channel, for example, fluid entering the vial through the central lumen and exiting the vial through the outer lumen. Such a channel can also be described as having a toros shape.

When the vial attached to the first transfer spike (B) is emptied of fluid, any fluid remaining in the vial attached to the second spike (C) . empties through the tube (E), through the valve assembly (A) and into the syringe. Both vials are emptied by this process, which allows fluid combination in the vials attached to the first transfer spike (B), the valve assembly (A) and the syringe. The vials can be any vessel generally acceptable to those of ordinary skill in the art; the suitability of a particular vessel for use in connection with this invention's device can readily be determined by ordinarily skilled artisans without undue experimentation, given the teachings of this invention. Since the vials are positioned on the device prior to their contents being released by piercing with a point, and since the mixing occurs within the device without having to remove the vials, the risk of the operator coming into contact with the contents of the vials or receptacle are reduced. This is especially valuable when such contents pose toxicity hazards to the operator. Further risk reduction can be accomplished by disposing the device without removing the empty fluid containers from it.

When the syringe plunger is infused upward, the fluids pass from the syringe, through the valve assembly (A) and into the third transfer spike (D) vial, so as to form a formulation comprising the fluids and the chemical composition. The first valve disc is then positioned by the positive pressure of the upward stroke such that it blocks fluid reflow into the first passage, connecting the valve assembly (A) and the first transfer spike (B). The second valve disc is positioned such that it does not then block fluid flow from the syringe through the valve assembly (A) and third transfer spike (D). Again, the device's operator can observe the mixing and can enhance it by agitating the device. The device is designed to permit fluid passage through its components without an excessive degree of turbulence, that is, without such turbulence that would significantly interfere with fluid passage and fluid and chemical composition combination. For example, with the steady downward aspiration of the plunger of a 10 cc syringe attached to the port, the complete contents of two 5-ml vials can be combined, and then infused into the receptacle, within one to two minutes.

The device's beveled points are designed to pierce the cover of a fluid container; its opening is intended to permit fluid to flow through the point. The size of the opening is generally large enough to permit unobstructed fluid flow, that is, flow not significantly inhibited by turbulence caused by fluid passage through the opening, but is not so large as to weaken the structure of the beveled point. Any structure capable of piercing the cover of a fluid container and allow fluid to flow through it from the attached vial and which is generally accepted in the art for such purposes, can be used in the device of this invention. The diameter of the channels, bores, passages and other conduits of the device is sufficiently large to permit fluid passage without a degree of turbulence that would significantly inhibit fluid passage, but which is otherwise consistent with inclusion in a hand-held device.

The device can further comprise one or more additional transfer spikes, for example. Such an additional spike can be connected in series with the first and second transfer spikes (B, C), preferably between the first and second spikes. This additional series connected spike preferably has a beveled point, double-lumened channel and an aperture at the end of the channel opposite the point to which a first end of an additional tube is connected. The other end of this additional tube is preferably connected to the eleventh aperture, of the second transfer spike (C). The additional spike preferably also has a passage having an aperture in the channel connected to another aperture to which a first end of an additional piece of tubing can be connected; the second end of the tubing is then preferably connected to the eighth aperture. Further additional transfer spikes can be connected in series between the first and second spikes (B, C).

Also provided herein is a formulation preparation kit which comprises: the device, a vial comprising a first fluid, a vial comprising a second fluid and a third vial, wherein the first and second fluids are combined by the device and wherein the fluid combination is then infused into the third vial so as to form a formulation comprising the fluid combination and the contents of the third vial.

Preferably, the third vial contains a chemical compound, in powder, slurry, liquid or other suitable form. "Chemical compounds" which can be formulated with the device of this invention can be a compound or composition of matter existing in a solid or fluid state and includes, but is not limited to, dried solid compounds, solids in a paste or slurry, suspended solids, or solutions containing dissolved solids. Compositions which can be used in connection with the device to prepare formulations include, but are not limited to: biologically active or pharmacologically active agents, dental agents, dyes, epoxies or chemical reagents. Preferably, the chemical composition is a biologically active agent, that is, a composition or composition of matter having some biological activity in an animal, or on an animal's cells in vitro. Biologically active agents include, but are not limited to: therapeutic, diagnostic, nutritional or prophylactic agents.

Presently, the preferred biologically active agent is a therapeutic agent, that is, an agent which can ameliorate, alleviate, lessen or inhibit the causes or symptoms of a disease, disorder or condition. Preferred therapeutic agents include, but are not limited to: anti-arthritic, anti-arrhythmic, antibacterial, anticholinergic, anticoagulant, antidiuretic, antidote, antiepileptic, antifungal, anti-inflammatory, antimetabolic, antimigraine, antineoplastic, antiparasitic, antipyretic, antiseizure, antisera, antispasmodic, analgesic, anesthetic, beta-blocking, biological response modifying, bone metabolism regulating, cardiovascular, diuretic, enzymatic, fertility enhancing, growth-promoting, hemostatic, hormonal, hormonal suppressing, hypercalcemic alleviating, hypocalcemio alleviating, hypoglycemic alleviating, hyperglycemic alleviating, immunosuppressive, immunoenhancing, muscle relaxing, neurotransmitting, parasympathomimetic, sympathomimetic, plasma extending, plasma expanding, psychotropic, thrombolytic and vasodilating agents. More preferably presently, the therapeutic agent is an antineoplastic agent, such as those selected from the group consisting of anthracycline antibiotics, vinca alkaloids, purine or pyrimidine derivatives and alkylating agents. Most preferably, presently, the antineoplastic agent is the anthracycline antibiotic doxorubicin.

Alternatively, the biologically active agent can be a diagnostic agent, that is, an agent which can aid in the identification of a disease, its causes or symptoms. Useful diagnostic agents include, but are not limited to: labeled antibodies, dyes, radioisotopes, or arteriographic, venographic, CT scan enhancing, x-ray contrast or NMR contrast agents. The biologically active agent can also be a nutritional agent, that is, an agent which can supply energy and raw materials for the building of tissues in an animal, or can aid in the maintenance of bodily functions or processes. Useful nutritional agents include, but are not limited to: food supplements, vitamins or electrolytes.

The biologically active agent can further be a prophylactic agent, that is, an agent which can aid in the prevention of a disease, such as by potentiating immune responses in an animal to the causative agent of the disease. Useful prophylactic agents include, but are not limited to antigens, antibodies and vaccines. The chemical composition can also include other agents useful in the medical field, such as a dental adhesive, e.g., Etchant, anesthetic or antibiotic.

Ionizable biologically active agents are preferred chemical compositions for the preparation of liposomal formulations using the device of this invention. When ionizable biologically active agents are used, the second fluid is preferably an aqueous buffer having a second pH, which is basic with respect to the first pH when the ionizable biologically active agent is cationic, end which is acidic with respect to the first pH when the agent is artionic. Combination of this buffer with the liposome suspension can establish a pH gradient across the liposome's lipid bilayer. Ionizable biologically active agents can be loaded into liposomes by such gradients (see Bally et al., U.S. Pat. No. 5,077,056, the contents of which are incorporated herein by reference).

Preferably, but not necessarily, the first fluid comprises a liposome which comprises an aqueous buffer having a first pH; more preferably, the liposome is a unilamellar liposome and the aqueous buffer is a citric acid buffer. Preferably, the second fluid is an aqueous buffer having a second pH which is acidic or basic with respect to the first pH and wherein the third vial comprises an ionizable biologically active agent.

Liposomes are self-assembling structures comprising one (unilamellar liposomes) or more (oligolamellar or multilamellar liposomes) lipid bilayers. The liposome employed in connection with the device of this invention can be unilamellar, oligolamellar or multilamellar, but is presently preferred to be a unilamellar liposome. Each liposomal lipid bilayer surrounds a compartment comprising an aqueous medium, and each contains two opposing monolayers of amphipathic lipid molecules. The amphipathic lipid molecules which make up lipid bilayers comprise a polar (hydrophilic) headgroup region covalently linked to one or two non-polar (hydrophobic) acyl chains. It is believed that the energetically unfavorable contact between the hydrophobic acyl chains and the aqueous medium causes the lipid molecules to rearrange such that the polar headgroups are oriented towards the surrounding aqueous medium, while the acyl chains reorient towards the interior of the bilayer. The net result is an energetically stable structure in which the acyl chains are effectively shielded from coming into contact with the aqueous medium.

Liposomes may be produced by a variety of methods (for a review, see, e.g., Cullis et al., in: *Liposomes, From Biophysics to Therapeutics* M. J. Ostro, ed.), Marcel Dekker, pp. 39–72 (1987)). Bangham's procedure (J. Mol. Biol. 13:238–252 (1965)) produces ordinary multilamellar vesicles (MLVs). Lenk et al. (U.S. Pat. Nos. 4,522,803, 5,030,453 and 5,169,637), Fountain et al. (U.S. Pat. No. 4,588,578) and Cullis et al. (U.S. Pat. No. 4,975,282) disclose methods for producing multilamellar liposomes having substantially equal interlamellar solute distribution in each of their aqueous compartments. Unilamellar vesicles can be produced from MLVs by sonication (see Papahadjopoulos et al., Biochem. Biophys. Acta. 135:624 (1968)) or extrusion (Cullis et al. (U.S. Pat. No. 5,008,050) and Loughrey et al. (U.S. Pat. No. 5,059,421)). Janoff et al. (U.S. Pat. No. 4,721,612) and Bolcsak et al. (U.S. Pat. No. 5,100,662) describe the use of sterols for the preparation of liposomes having enhanced stability. These disclosures are incorporated herein by reference.

In one preferred embodiment of the invention, the formulation preparation kit comprises: a doxorubicin-containing receptacle; a vial comprising an aqueous suspension of a unilamellar liposome, the liposome, in turn, containing an aqueous citrate buffer of about pH 4.0; and a vial comprising a second aqueous buffer having a pH greater than 4.0, preferably about 7.0 to 7.5. The doxorubicin, the liposome and the second aqueous buffer are combined so that doxorubicin is entrapped in the liposome and the liposome is suspended in the buffer.

Further provided herein is a method of preparing a formulation comprising fluids and a chemical composition with the device of this invention, which comprises attaching a container comprising a fluid to the first transfer spike (A), a container comprising a fluid to the second transfer spike (B) and a receptacle containing the composition to the infusion spike (I). A syringe is inserted into the port (G), and the plunger of the syringe is aspirated downward, so that fluid passes from the vials, through the first valve entity of the valve assembly, and into the syringe. Fluid or air cannot pass through the second valve entity of the valve assembly when the syringe plunger is drawn downward, and these cannot then reflux through the first valve entity. The syringe's plunger is then pushed upward so that the fluids flow into the receptacle. Fluid or air cannot pass through the first valve entity of the valve assembly when the syringe plunger is pushed upward, and does not reflux through the second valve entity. In a presently preferred embodiment of the invention, the method uses: (1) a first fluid that is an aqueous liposome suspension, preferably a unilamellar liposome having a pH of about 4.0; (2) a second fluid that is an aqueous buffer, preferably a buffer having a pH greater than 4.0, such as from pH 7.0 to pH 7.5; and (3) a receptacle containing an ionizable biologically active agent, preferably, doxorubicin. The liposome, aqueous buffer and the ionizable biologically active agent are combined so that the biologically active agent is associated with the liposome, that is, it is entrapped in an aqueous compartment of the liposome or associated with a lipid bilayer, and the liposome is suspended in the aqueous. The device of this invention can be manipulated by end users of the desired composition-fluid formulations prepared to combine fluids in definable, reproducible amounts and proportions, with chemical compositions if necessary, immediately prior to use of the formulations. Formulations can be made aseptically, such that contact between the device's operator and the fluids is avoided.

The following example further describes the invention. However, those of ordinary skill in the art will readily understand that the example is merely illustrative of the invention as defined in the claims which follow thereafter.

EXAMPLES

Example 1

Preparation of Liposomal Doxorubicin

A preparation kit containing the device of this invention, sterilized, a vial containing egg phosphatidylcholine/cholesterol (EPC/Chol)liposomes (vial #1), a vial containing an aqueous buffer (vial #2) and a vial (vial #3) containing a doxorubicin hydrochloride/saline solution was used. Also used was a disposable syringe Protective caps were removed from the first and second transfer spikes ((B) and (C)), following which the vials were attached thereto, the beveled points piercing the covers of the vials. A protective cap was removed from the syringe port (E), and a Luer-Lok syringe was attached thereto. The syringe plunger was then drawn downward, completely emptying the contents of vials 1 and 2 into the syringe. The device was gently shaken to aid in mixing of the fluids in the syringe. A protective cap was next removed from the third transfer spike (D), to which the doxorubicin-containing vial was attached, piercing the receptacle's cover. The syringe's plunger was then infused upward, emptying the syringe's contents in the vial #3; this resulted in loading of the doxorubicin into the liposome. The receptacle was then removed, and the device, with vials 1 and 2 remaining attached thereto; was disposed of.

What is claimed is:

1. A formulation preparation device which comprises:
   (a) a valve assembly comprising a first passage, a second passage and a third passage, a main body having three apertures and a central cavity within the main body comprising a first and second valve disc, wherein the apertures in the main body access the central cavity, wherein each of the first, second and third passages has two open ends, wherein one end of each of the passages is connected to a different aperture in the main body and wherein the other end of each of the passages is connected to an aperture or opening in the device;
   (b) a first transfer spike body comprising:
      (i) a beveled point containing an opening; and,
      (ii) a toros-shaped conduit having an inner channel and an outer channel, wherein each of the inner and outer channels has two open ends, wherein a first end of each of the inner and outer channels is connected to the beveled point opening and wherein the other end of the outer channel is connected to the valve assembly's first passage; and,
   (c) a second transfer spike body comprising:
      (i) a beveled point having an opening; and
      (ii) a toros-shaped conduit having an inner channel and an outer channel, wherein each of the inner and outer channels has two open ends, wherein a first end of each of the inner and outer channels is connected to the beveled point opening, and wherein a hydrophobic air filter is sealed into the second open end of the inner channel;
   (d) a tube having open ends, wherein one end of the tube is connected to the first transfer spike body at the open end of the first transfer spike body's inner channel and wherein the other end of the tube is connected to the second transfer spike body at the open end of the second transfer spike body's outer channel;
   (e) a syringe port comprising an opening and a luer lock fitting;
   (f) a passage connecting the syringe port and the valve assembly, wherein one end of the passage is connected to the port's opening and the other end of the passage is connected to the open end of the valve assembly assembly's second passage;
   (g) an infusion spike body comprising:
      (i) a beveled point containing an opening; and
      (ii) a conduit connecting the opening and the valve assembly, wherein one end of the conduit is connected to the point's opening and wherein the other end of the conduit is connected to an open end of the valve assembly's third passage; and,
   (h) a sterilizable, gripable housing having a plurality of surfaces, wherein the housing contains the valve assembly, the hydrophobic air filter and the tube and wherein the beveled points and syringe port project from one or more of the housing's surfaces, whereby when a syringe is inserted into the syringe port and the syringe plunger is aspirated downward, the first and second valve discs are positioned in the valve assembly's central cavity such that fluid flow is permitted between the first transfer spike body and the syringe port and not between the first transfer spike body and the infusion spike body; and whereby when the syringe plunger is infused upward, the first and second valve discs are positioned in the valve assembly central cavity such that fluid flow is permitted between the syringe port and the infusion spike body and not between the syringe port and the first transfer spike body.

2. The device of claim 1, wherein each of the spike bodies comprises a collar positioned on the spike bodies between the beveled point and the outer surface of the housing.

3. A formulation preparation kit which comprises:
   (I) the device of claim 1;
   (ii) a first vial comprising a first fluid;
   (iii) a second vial comprising a second fluid; and
   (iv) a third vial,
wherein when the first and second transfer vials are attached to the first and second spike bodies, the third vial is attached to the infusion spike body and a syringe attached to the syringe port is operated in connection with the device, the first and second fluids are combined by the device so as to form a fluid combination and the fluid combination is then injected by the device into the third vial so as to form a formulation comprising the fluid combination and the contents of the third vial.

4. The preparation kit of claim 3, wherein the third vial contains a a biologically active agent, diagnostic agent, nutritional agent, prophylactic agent, dental agent, cosmetic, dye, epoxy or chemical reagent.

5. The preparation kit of claim 4, wherein the biologically active agent is a therapeutic agent selected from the group consisting of anti-arthritic, anti-arrhythmic, antibacterial, anticholinergic, anticoagulant, antidiuretic, antidote, antiepileptic, antifungal, anti-inflammatory, antimetabolic, antimigraine, antineoplastic, antiparasitic, antipyretic, antiseizure, antisera, antispasmodic, analgesic, anesthetic, beta-blocking, biological response modifying, bone metabolism regulating, cardiovascular, diuretic, enzymatic, fertility enhancing, growth-promoting, hemostatic, hormonal, hormonal suppressing, hypercalcemic alleviating, hypocalcemic alleviating, hypoglycemic alleviating, hyperglycemic alleviating, immunosuppressive, immunoenhancing, muscle relaxing, neurotransmitting, parasympathomimetic, sympathomimetic, plasma extending, plasma expanding, psychotropic, thrombolytic and vasodilating agents.

6. The preparation kit of claim 5, wherein the therapeutic agent is an antineoplastic agent selected from the group consisting of anthracycline antibiotics, vinca alkaloids, purine or pyrimidine derivatives or alkylating agents.

7. The preparation kit of claim 3, wherein the first fluid comprises a liposome which comprises an aqueous buffer having a first pH.

8. The preparation kit of claim 7, wherein the liposome is a unilamellar liposome.

9. The preparation kit of claim 7, wherein the aqueous buffer is a citric acid buffer.

10. The preparation kit of claim 7, wherein the second fluid is an aqueous buffer having a second pH which is acidic or basic with respect to the first pH and wherein the third vial contains an ionizable biologically active agent.

11. The preparation kit of claim 10, wherein the first fluid comprises a unilamellar liposome having an average diameter of greater than about 50 nm and comprising a citric acid buffer having a pH of from about 3.5 to about 4.5, wherein the second fluid comprises a carbonate buffer, wherein the third vial comprises an ionizable biologically active agent and wherein the agent, the liposome and the carbonate buffer are combined by the device so that the liposome is suspended in the carbonate buffer and the agent is entrapped in the liposome.

12. The preparation kit of claim 11, wherein the biologically active agent is an anthracycline antibiotic antineoplastic agent selected from the group consisting of doxorubicin, daunorubicin and epirubicin.

13. The preparation kit of claim 12, wherein the anthracycline is doxorubicin.

14. A method of preparing a formulation with the device of claim 1 which comprises (a) attaching a first vial containing a first fluid to the first transfer spike body, a second vial containing a second fluid to the second transfer spike body and a third vial to the infusion spike body;

(b) inserting a syringe into the syringe port and aspirating the plunger of the syringe downward so that:

(i) fluid flows from the first vial through the valve assembly, into the syringe port and then through the port's opening into the syringe; and, (ii) fluid flows from the second vial through the tube then through the inner channel of the first transfer spike body and then into the first vial.

whereby the contents of the first and second vials are combined; and, c) infusing the plunger of the syringe upward so that the fluid combination flows from the syringe, through the valve assembly, and then through the infusion spike's beveled point opening into the third vial so as to form a formulation comprising the combination and the contents of the third vial.

15. The method of claim 14, wherein the first vial comprises a unilamellar liposome having an average diameter of greater than about 50 nm and a citric acid buffer having a pH of from about 3.5 to about 4.5, wherein the second vial comprises a carbonate buffer, wherein the third vial comprises doxorubicin and wherein the doxorubicin, the liposome and the carbonate buffer are combined so that the liposome is suspended in the carbonate buffer and the doxorubicin is entrapped in the liposome.

\* \* \* \* \*